United States Patent
Seo et al.

(10) Patent No.: US 11,377,633 B2
(45) Date of Patent: Jul. 5, 2022

(54) MEDIUM SUPPLEMENT FOR HIGH-YIELD INDUSTRIAL CULTURE OF FASTIDIOUS ANAEROBES AND MEDIUM COMPOSITION CONTAINING THE SAME

(71) Applicant: ENTEROBIOME INC., Goyang-si (KR)

(72) Inventors: Jae-Gu Seo, Gimpo-si (KR); Do-Kyung Lee, Seoul (KR)

(73) Assignee: ENTEROBIOME INC., Goyang-si (KR)

( * ) Notice: Subject to any disclaimer, the term of this patent is extended or adjusted under 35 U.S.C. 154(b) by 0 days.

(21) Appl. No.: 17/431,212

(22) PCT Filed: Dec. 28, 2020

(86) PCT No.: PCT/KR2020/019214
§ 371 (c)(1),
(2) Date: Aug. 16, 2021

(87) PCT Pub. No.: WO2022/102866
PCT Pub. Date: May 19, 2022

(65) Prior Publication Data
US 2022/0145239 A1    May 12, 2022

(30) Foreign Application Priority Data

Nov. 11, 2020   (KR) ........................ 10-2020-0150111

(51) Int. Cl.
*C12N 1/20*     (2006.01)
*C12R 1/01*     (2006.01)

(52) U.S. Cl.
CPC ............ *C12N 1/20* (2013.01); *C12N 2500/02* (2013.01); *C12N 2500/10* (2013.01); *C12N 2500/32* (2013.01); *C12N 2500/34* (2013.01); *C12N 2500/38* (2013.01); *C12N 2500/74* (2013.01); *C12R 2001/01* (2021.05)

(58) Field of Classification Search
CPC .. C12N 1/20; C12N 2500/02; C12N 2500/10; C12N 2500/32; C12N 2500/34
See application file for complete search history.

(56) References Cited

U.S. PATENT DOCUMENTS 10,988,509 B2 * 4/2021 Belzer ...................... C12N 1/20
2018/0094233 A1   4/2018 Belzer et al.

FOREIGN PATENT DOCUMENTS

| KR | 10-2013-0021920 A | 3/2013 | |
|----|-------------------|--------|---|
| KR | 10-2015-0133646 A | 11/2015 | |
| KR | 10-1809172 B1 | 12/2017 | |
| KR | 10-2018-0018524 A | 2/2018 | |
| KR | 10-2020-0041280 A | 4/2020 | |
| WO | WO-2018106844 A1 * | 6/2018 | ........... A61K 9/0053 |

OTHER PUBLICATIONS

"Hexose", https://en.wikipedia.org/wiki/Hexose (Year: 2022).*
"N-Acetylhexosamine", https://pubchem.ncbi.nlm.nih.gov/compound/N-Acetylhexosamine (Year: 2022).*
International Search Report of PCT/KR2020/019214 dated Aug. 4, 2021 [PCT/ISA/210].
Written Opinion of PCT/KR2020/019214 dated Aug. 4, 2021 [PCT/ISA/237].
Korean Intellectual Property Office, Office Action in Application No. 10-2020-0150111 dated Jan. 3, 2021.

* cited by examiner

*Primary Examiner* — Ruth A Davis
(74) *Attorney, Agent, or Firm* — Sughrue Mion, PLLC (57) ABSTRACT

A medium supplement for high-yield culture of anaerobes is disclosed. The medium supplement includes N-acetylhexosamine, L-aspartic acid, L-cysteine and cobalamin. A culture medium including the supplement and a culture method using the culture medium are also disclosed. It is possible to provide an innovative method which is capable of achieving high-concentration culture of anaerobes that are difficult to culture in high yield. The method is cost-effective, and in particular, is capable of culturing large amounts of fastidious aerobes suitable for use in food and pharmaceutical applications.

11 Claims, 7 Drawing Sheets

[Middle/late stage of culture]

[Initial stage of culture]

MEDIUM SUPPLEMENT FOR HIGH-YIELD INDUSTRIAL CULTURE OF FASTIDIOUS ANAEROBES AND MEDIUM COMPOSITION CONTAINING THE SAME

CROSS REFERENCE TO RELATED APPLICATIONS

This application is a National Stage of International Application No. PCT/KR2020/019214 filed on Dec. 28, 2020, claiming priority based on Korean Patent Application No. 10-2020-0150111 filed on Nov. 11, 2020.

TECHNICAL FIELD

The present invention relates to a novel medium supplement for high-yield culture of fastidious anaerobes, a medium composition containing the same, and a method for high-yield culture of fastidious anaerobes using the same, and more particularly to a medium supplement, a medium composition and a culture method, which are capable of producing large amounts of fastidious anaerobes including *Akkermansia muciniphila* and are suitable for pharmaceutical and food applications.

BACKGROUND ART

The term "human microbiome" refers to the microbial communities colonizing the human body and the genomes of these microbial communities. The microbiome has attracted a lot of attention as it has been found to be closely related to human health.

With the rapid development of research techniques in the field of biotechnology, such as germ-free animal models, next-generation sequencing (NGS), and multi-omics analysis, it became possible to study the relationship between the function of the microbiome and diseases in addition to analyzing the composition and structure of gastrointestinal microbes, and thus more research results have been published. Microbiome therapeutics or pharmabiotics (medical probiotics) have recently attracted attention because they can be used as alternative therapeutics for infectious diseases, immune diseases, and metabolic diseases against which effective therapeutics are not available. Microbiome therapeutics or pharmabiotics are expected to be advantageously applicable to various intractable diseases if they can be commercialized through mass production.

Since the inside of the human intestine is in an anaerobic state, most of the anaerobes that make up the microbiome are anaerobic microorganisms. These anaerobes are difficult to produce in high concentrations and large amounts for commercial purposes, because carbon and nitrogen sources available for these anaerobes are very limited and these anaerobes have the physiological property of being strictly anaerobic, which is extremely sensitive to oxygen. Strictly anaerobic microorganisms are extremely difficult to culture and are more difficult to obtain in high biomass yields.

For example, *Akkermansia muciniphila*, which inhabits the mucous layer of the large intestine and is a promising pharmabiotic candidate, can be cultured by adding hog gastric mucin (extracted from porcine stomach) as carbon and nitrogen sources to media (Derrien et al., 2004). In addition, *Akkermansia muciniphila* strains are also cultured on Columbia broth (CB) and brain heart infusion (BHI) broth. These media all contain animal-derived components, and furthermore, mostly show lower culturability than mucin-based media, and thus allow the strains to grow up to a final optical density equal to only half of a final optical density obtainable by the mucin-based media.

Since animal-derived components may contain contaminants of viral or bacterial origin or may contain allergens, antigenic peptides or other undesirable products, these components are recognized to be unsuitable for use in the culture of anaerobes for food or pharmaceutical uses in humans. Despite considerable efforts up to date, conventional media for culturing anaerobes are difficult to prepare, are expensive, and furthermore, cannot achieve high-yield culture of anaerobes. For these reasons, these media have limitations that cannot be used for industrial purposes other than special research purposes.

DISCLOSURE OF INVENTION

Technical Problem

The present invention has been conceived to overcome the above-described limitations or problems, and an object of the present invention is to provide a medium supplement and a medium composition, which may produce anaerobes to be used as microbiome therapeutics or pharmabiotics in high yield in a stable manner over a long period of time during industrial mass culture of these anaerobes so as to be suitable for use as pharmaceuticals, foods or feeds.

Another object of the present invention is to provide a culture method capable of economically culturing fastidious anaerobes to a high final optical density.

Solution to Problem

One aspect of the present invention for achieving the above objects is directed to a medium supplement for high-yield culture of anaerobes, the medium supplement including N-acetylhexosamine, L-aspartic acid, L-cysteine and cobalamin.

The medium supplement of the present invention may include 5 g/L of N-acetylhexosamine, 8 g/L of L-aspartic acid, 0.5 g/L of L-cysteine, and 0.0001 to 0.005 g/L of cobalamin.

The anaerobes may be human gastrointestinal strict-anaerobic microorganisms, including, but are not necessarily limited to, *Faecalibacterium prausnitzii, Anaerostipes caccae, Akkermansia muciniphila, Butyricicoccus pullicaecorum, Roseburia inulinivorans, Roseburia hominis*, or *Bifidobacterium longum*.

Another aspect of the present invention for achieving the above objects is directed to a medium composition for high-yield culture of anaerobes, the medium composition containing: plant peptone; yeast extract; potassium phosphate dibasic; as a carbon source, fructose and lactose; and as a supplement, N-acetylhexosamine, an amino acid mixture of L-aspartic acid and L-cysteine, and cobalamin.

The medium composition for high-yield culture of anaerobes according to the present invention may contain 2.5 g/L of fructose, 2.5 g/L of lactose, 20 g/L of plant peptone, 10 g/L of yeast extract, 2.5 g/L of potassium phosphate dibasic, 5 g/L of N-acetylhexosamine, 8 g/L of L-aspartic acid, 0.5 g/L of L-cysteine, and 0.0001 to 0.005 g/L of cobalamin.

The plant peptone may be selected from the group consisting of soy peptone, wheat peptone, cotton peptone, pea peptone, broadbean peptone, lupin peptone, and potato peptone, but is not necessarily limited thereto.

Still another aspect of the present invention for achieving the above objects is directed to a method for high-yield culture of anaerobes, the method including inoculating anaerobes into the above-described medium composition and culturing the inoculated anaerobes under anaerobic conditions.

The culturing of the inoculated anaerobes may be performed under conditions of a pH of 6.6 to 7.0, a culture temperature of 35 to 39° C., an agitation speed of 40 to 50 rpm, a nitrogen saturation degree of 80 to 90%, a hydrogen saturation degree of 0 to 5%, and a carbon dioxide saturation degree of 5 to 20%.

In the method for high-yield culture of anaerobes according to the present invention, the cultured anaerobes may reach a cell density corresponding to a viable cell count of $10^{10}$ CFU/mL or more as measured by a plate count method.

Advantageous Effects of Invention

According to various embodiments of the present invention, anaerobes to be used as microbiome therapeutics or pharmabiotics may be stably produced in high yield during industrial mass culture of these anaerobes so as to be suitable for use as pharmaceuticals, foods or feeds.

According to the medium supplement and medium composition of the present invention, *Akkermansia muciniphila*, which is a promising pharmabiotic candidate but is a fastidious strain which could not be produced in large amounts because being killed by even a trace amount of oxygen due to extremely high sensitivity to oxygen, may be cultured in a high concentration so as to be suitable for pharmaceutical or food applications.

The anaerobes cultured in high yield using the medium supplement or medium composition of the present invention may be widely used for pharmabiotics, lactic acid bacteria preparations, dairy products, and probiotics.

BRIEF DESCRIPTION OF DRAWINGS

The above and other objects, features, and advantages of the present invention will be more clearly understood from the following detailed description taken in conjunction with the accompanying drawings, in which:

FIG. 6 depicts graphs showing a growth curve (FIG. 6A) and a change in pH (FIG. 6B) of an *Akkermansia muciniphila* strain as a function of culture time in a fructose-containing medium of the present invention;

FIG. 7 depicts graphs showing a growth curve (FIG. 7A) and a change in pH (FIG. 7B) of an *Akkermansia muciniphila* strain as a function of culture time in a maltose-containing medium of the present invention; and FIG. 8 depicts graphs showing a growth curve (FIG. 8A) and a change in pH (FIG. 8B) of an *Akkermansia muciniphila* strain as a function of culture time when the strain was cultured using high-purity nitrogen gas alone in a fructose-containing medium of the present invention.

MODE FOR THE INVENTION

The present invention will be described in detail below with reference to the accompanying drawings.

As used herein, the term "medium" or "culture medium" refers to a solid, semisolid or liquid medium containing all of the nutrients and necessary physical growth parameters necessary for microbial growth or proliferation.

As used herein, the term "culture" or "growth" of microorganisms means multiplying microbial organisms by letting them reproduce in a predetermined culture medium under conditions conducive for their growth.

As used herein, the term "supplement" of medium refers to an additive consisting of selected components to promote the growth, proliferation or other characteristics of one or more desired anaerobes.

As used herein, the term "anaerobes" refers to microorganisms that do not grow in the presence of oxygen due to their sensitivity to oxygen. Anaerobes may include strict or obligate anaerobic microorganisms and facultative anaerobic microorganisms.

As used herein, the term "includes", "comprises", "contains" and variations thereof do not have a limiting meaning where these terms appear in the description and claims.

In addition, in the present specification, the recitation of numerical ranges by endpoints includes all numbers subsumed within the range (for example, 1 to 5 includes 1, 1.5, 2, 2.5, 3, 3.5, 4, 4.5, etc.).

One aspect of the present invention is directed to a medium supplement for high-yield culture of anaerobes, the medium supplement including N-acetylhexosamine, L-aspartic acid, L-cysteine and cobalamin. The medium supplement of the present invention may include 5 g/L of N-acetylhexosamine, 8 g/L of L-aspartic acid, 0.5 g/L of L-cysteine, and 0.0001 to 0.005 g/L of cobalamin.

The medium supplement of the present invention is used mainly for culture of anaerobes, and these anaerobes are gastrointestinal strict anaerobic microorganisms.

Examples of these anaerobes include, but are not limited to, *Faecalibacterium prausnitzii, Anaerostipes caccae, Akkermansia muciniphila, Butyricicoccus pullicaecorum, Roseburia inulinivorans, Roseburia hominis,* or *Bifidobacterium longum*.

Figure 1:
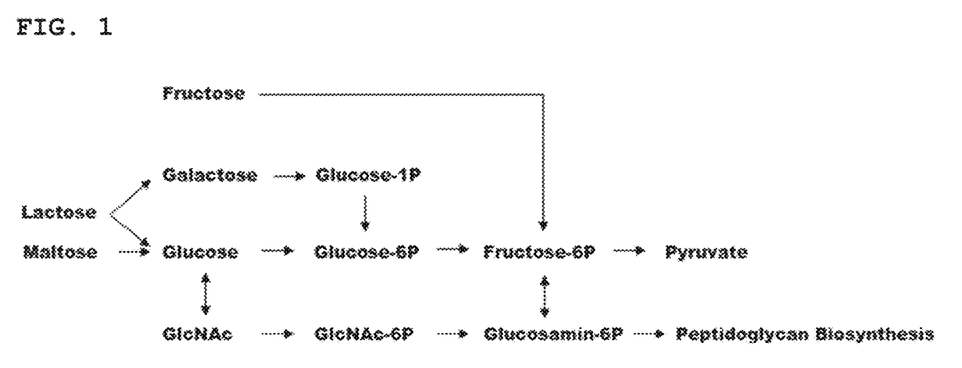
FIG. 1 is a schematic view showing the process of carbon metabolism in an *Akkermansia muciniphila* strain.

The medium supplement for high-yield culture of anaerobes according to the present invention includes N-acetylhexosamine N-acetylhexosamine may include N-acetylglucosamine (GlcNAc) or N-acetylglactosamine (GalNAc), preferably N-acetylglucosamine (GlcNAc). FIG. 1 is a schematic view showing the process of carbon metabolism in *Akkermansia muciniphila*. Referring to FIG. 1, since *Akkermansia muciniphila* has the enzyme β-galactosidase that converts lactose into galactose and glucose and the enzyme α-glucosidase that converts maltose into glucose, carbon sources such as lactose, maltose, and fructose are all used to form the high-energy molecule ATP through glycolysis. N-acetylglucosamine (Glc-NAc) that is externally supplied is used for cell wall synthesis (peptidoglycan biosynthesis) and energy metabolism, and N-acetylglucosamine is metabolized to produce ammonia, which neutralizes the cytoplasm and may also function as a nitrogen source. In addition to N-acetylglucosamine (Glc-NAc), N-acetylgalactosamine (Gal-NAc) may be further added.

The N-acetylhexosamine may be included in an amount ranging from about 2.5 to 5 g/L Amino acids are important for maintaining the metabolic function of cells cultured in cell culture media. In order to sustain good growth during high-concentration culture of anaerobes, an external protein source is essential. The present inventors have found that a combination of aspartic acid and cysteine among various amino acids is very effective as a protein source or nitrogen source for anaerobes Amino acids include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-hydroxyproline, L-serine, L-threonine, L-tryptophan, L-tyrosine, and L-valine, and mucins that can be degraded by *Akkermansia muciniphila* are characterized by repetitive amino acid sequences rich in serine, threonine, proline and cysteine. However, according to the present invention, *Akkermansia muciniphila* may be grown in high yield by adding aspartic acid and cysteine among these amino acids. Aspartic acid and cysteine may exist in D- and L-forms.

Figure 2:
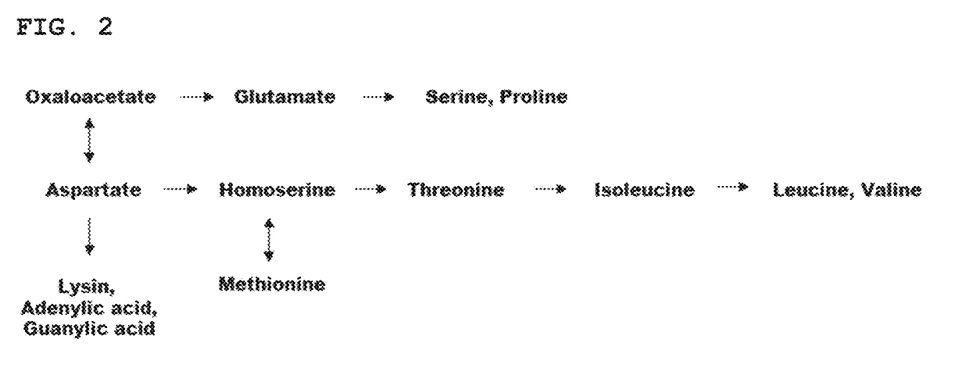
FIG. 2 is a schematic view showing a process in which various amino acids are biosynthesized from aspartic acid.
Figure 3:
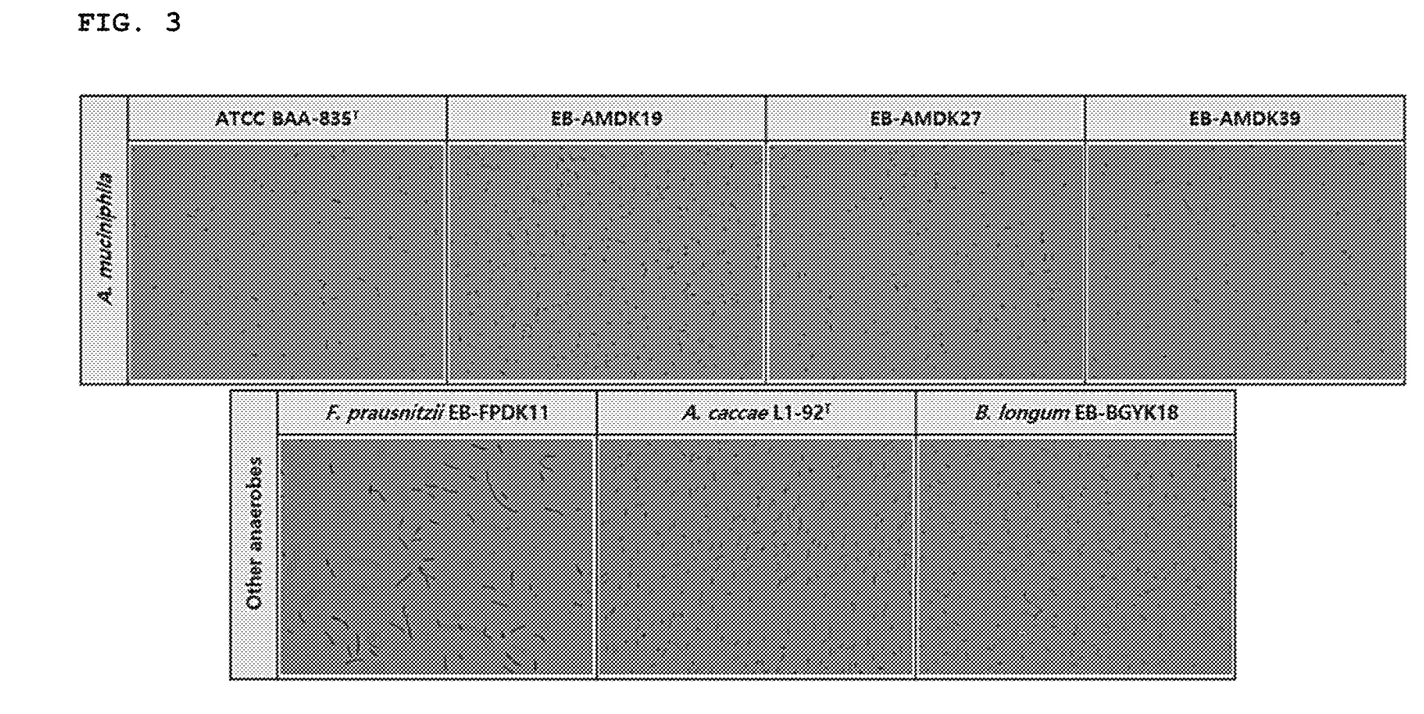
FIG. 3 depicts images showing the cell morphologies of different strains of anaerobes cultured in media containing the medium supplement of the present invention.

FIG. 2 is a schematic view showing a process in which various amino acids are biosynthesized from aspartic acid. Referring to FIG. 2, aspartic acid may be converted to homoserine which is an intermediate in the biosynthesis of threonine and methionine, and various amino acids including serine and proline may be biosynthesized from aspartic acid. In addition, aspartic acid may produce pentose phosphates and nicotinamide adenine dinucleotide phosphate (NADPH) necessary for the synthesis of nucleic acids, fatty acids and glutathione (a very important antioxidant in some bacteria), thereby improving resistance to acid stress. In addition, the biosynthesis of lysine and threonine from aspartic acid helps the growth of some microbial species, and the intake of aspartic acid may increase the diversity of gastrointestinal microbiota.

The medium supplement of the present invention may include aspartic acid and cysteine in amounts in the ranges of, for example, about 4 to 8 g/L and about 0.5 to 1 g/L, respectively.

The medium supplement of the present invention includes cobalamin, that is, vitamin B12. Cobalamin is a cofactor that is used by cells. When a culture medium contains no mucin, it requires a significant amount of cobalamin so that anaerobes grow at high density. Cobalamin may include compounds equivalent to cobalamin. The term "cobalamin" may include compounds equivalent to cobalamin. For example, the term "cobalamin" may include cyanocobalamin, methyl cobalamin, adenosyl cobalamin, hydroxyl cobalamin and other functionally equivalent chemicals. The culture medium supplement of the present invention may include cobalamin in an amount ranging from about 0.0001 to 0.005 g/L.

Vitamins include biotin, choline chloride, folic acid, myoinositol, niacinamide, pyridoxine HCl, D-pantothenic acid (hemiCa), riboflavin, thiamine HCl, etc. However, when cobalamin is added to a medium, the relative abundance of anaerobes is increased, and even if other vitamins are added, the effect of addition of these vitamins does not significantly differ from the effect of addition of cobalamin alone. The genome analysis of *Akkermansia muciniphila* indicated that most strains, including an ATCC BAA-835 strain and an EB-AMDK19 strain, have genes related to biosynthesis of group B vitamins (B1, B2, B3, B5, B6, B7, and B9), but do not have genes related to biosynthesis of vitamin B12. In addition, in *Akkermansia muciniphila*, cobalamin may act as an important coenzyme in the synthesis of propionate from succinate.

Another aspect of the present invention is directed to a medium composition for high-yield culture of anaerobes, the medium composition containing the medium supplement of the present invention.

A basal medium for preparing the medium composition for high-yield culture of anaerobes according to the present invention is preferably a liquid medium for the purpose of industrial production by mass cultivation. This basal medium may be a medium containing plant peptone, yeast extract and potassium phosphate dibasic.

The medium composition for high-yield culture of anaerobes according to the present invention is based on a medium containing plant peptone, yeast extract and potassium phosphate dibasic, and contains, as a carbon source, fructose and lactose, and as a supplement, N-acetylhexosamine, an amino acid mixture of L-aspartic acid and L-cysteine, and cobalamin.

The medium composition of the present invention is suitable for culture of anaerobes, particularly strict anaerobic microorganisms. Non-limiting examples of strict anaerobic microorganisms include, but are not necessarily limited to, *Faecalibacterium prausnitzii, Anaerostipes caccae, Akkermansia muciniphila, Butyricicoccus pullicaecorum, Roseburia inulinivorans, Roseburia hominis,* or *Bifidobacterium longum*. The medium composition of the present invention is particularly suitable for culturing the genus *Akkermansia*, specifically *Akkermansia muciniphila*, in high yield on an industrial scale.

The medium composition for high-yield culture of anaerobes according to the present invention may contain 20 g/L of plant peptone, 10 g/L of yeast extract, 2.5 g/L of potassium phosphate dibasic, 2.5 g/L of fructose, 2.5 g/L of lactose, 5 g/L of N-acetylhexosamine, 8 g/L of L-aspartic acid, 0.5 g/L of L-cysteine, and 0.0001 to 0.005 g/L of cobalamin.

The medium composition for high-yield culture of anaerobes according to the present invention may contain plant peptone. The plant peptone is a plant protein hydrolysate. It may be derived from any plant. The plant peptone may be, for example, selected from the group consisting of soy peptone, wheat peptone, cotton peptone, pea peptone, broadbean peptone, lupin peptone, and potato peptone. The plant peptone may be contained in an amount of, for example, about 15 to 20 g/L.

The medium composition for high-yield culture of anaerobes according to the present invention contains yeast extract. When yeast extract is added, an increase in the protein source may further increase the growth of anaerobes on the non-animal derived medium. The yeast extract may be a yeast autolysate, an ultrafiltered yeast extract or a synthetic yeast extract. The concentration of the yeast extract may be 5 g/L to 10 g/L, for example, about 10 g/L.

The medium composition of the present invention further contains a phosphate-containing component such as $Na_2HPO_4$, $K_2HPO_4$ or $KH_2PO_4$. This component is added to the cell culture medium composition to maintain isotonic conditions and prevent osmotic imbalance. The pH of the medium composition of the present invention is maintained within the range of 6.5 to 8.0, preferably 6.0 to 7.0, more preferably about 6.8±1.

The medium composition for high-yield culture of anaerobes according to the present invention may contain fructose and lactose as a carbon source and as an energy source, and may optionally further contain maltose. The concentration of fructose or maltose may be 2.5 g/L to 5.0 g/L, for example, about 2.5 g/L.

Glucose may also be contained as a carbon source, but when glucose is added, it does not last long although inducing exponential growth of microorganisms. In addition, glucose may be supplied by degradation of lactose linked to galactose by β(1→4)-glycosidic bonds, and N-acetylglucosamine and glucose are interchangeable in the metabolic pathway. For these reasons, a combination of fructose and lactose is more preferable than glucose.

In the present invention, the culture medium may be provided in the form of a powder or concentrate, also generally referred to as "powdered medium" or "concentrated medium", which includes a plurality of components or may be combined with a predetermined volume of water to provide a liquid medium with desired concentrations of the particular components. This powdered medium or concentrated medium may be dissolved in suitable water, normally sterile water, before use.

As used herein, the term "medium" or "medium composition" includes both the final media having components at concentrations suitable for culturing anaerobes, and powdered or concentrated media suitable for dilution.

The culture medium of the present invention may optionally contain a reducing agent for culture of anaerobes. Suitable reducing agents may promote the growth of anaerobes by lowering the oxidation-reduction potential of the culture medium and removing dissolved oxygen (oxygen scavenging). Examples of suitable reducing agents include, but are not necessarily limited to, sodium thioglycolate, L-cysteine, dithiothreitol, dithioerythritol, sodium sulfide ($Na_2S$), and combinations thereof.

According to one embodiment of the present invention, the medium of the present invention may be made anaerobic by substituting oxygen in the medium by a mixed gas obtained by mixing nitrogen ($N_2$), hydrogen ($H_2$) and carbon dioxide ($CO_2$) at a volume ratio of 100:0:0 to 90:5:5. According to one embodiment of the present invention, the pressure in the medium may be 0.1 to 0.3 atm, preferably 0.2 atm (0.02 MPa).

Still another aspect of the present invention is directed to a method for high-yield culture of anaerobes, the method including inoculating anaerobes into the above-described medium composition and culturing the inoculated anaerobes under anaerobic conditions.

Culture conditions for microorganisms may affect the growth rate of the microorganisms, as is well known to those skilled in the art. In the present invention, culture of the inoculated anaerobes may be performed under conditions of a pH of 6.6 to 7.0, a culture temperature of 35 to 39° C., an agitation speed of 40 to 50 rpm, a nitrogen saturation degree of 80 to 90%, a hydrogen saturation degree of 0 to 5%, and a carbon dioxide saturation degree of 5 to 20%.

In the present invention, culture of the anaerobes may be performed to reach a cell density corresponding to an optical density ($OD_{600}$) of 0.6 or more as measured at a wavelength of 600 nm using a microplate reader. At this time, the anaerobes may be cultured at high concentration so as to reach a cell density corresponding to a viable cell count of $10^{10}$ CFU/mL as measured by a plate count method.

The culture temperature for high-concentration culture of the anaerobes is preferably 35 to 39° C., particularly 36 to 38° C. During cultivation, the composition inoculated with the microbial suspension may be agitated. For example, the revolutions per minute (rpm) of the incubator may be 40 rpm to 50 rpm, but is not limited thereto. The culture period may be appropriately adjusted depending on the growth state of the anaerobes, but is generally about 20 to 100 hours, particularly about 24 to 48 hours.

According to one embodiment of the present invention, the medium of the present invention may be made anaerobic by substituting oxygen in the medium by a mixed gas obtained by mixing nitrogen ($N_2$), hydrogen ($H_2$) and carbon dioxide ($CO_2$) at a volume ratio of 90:5:5 to 80:0:20. Substitution of oxygen in the medium by the mixed gas is preferably performed for 30 seconds or more, most preferably 2 minutes, based on 1 mL of the medium volume.

*Akkermansia muciniphila* uses hydrogen ions for ATP synthesis in the metabolic pathway, and hydrogen ($H_2$) is important for anaerobic respiration by Ni-dependent hydrogenase under anaerobic conditions. Therefore, for high-concentration culture of an *Akkermansia muciniphila* EB-AMDK19 strain in the medium of the present invention, it is necessary to inject a mixed gas containing hydrogen or a gas containing carbon dioxide, which can dissolve in water and generate carbonic acid and hydrogen ions.

The present invention will be described in more detail with reference to examples, but the scope of the present invention is not limited to these examples. Unless otherwise specified, all parts and percentages mentioned in these examples are by weight, and all temperatures are expressed in degrees Celsius.

In addition, in the following examples, the concentration of anaerobes (amount of biomass produced) was determined by measuring the optical density of the culture medium at 600 nm using a spectrophotometer during the culture period. DOD was calculated as the difference in absorbance between the initial stage of culture and after 48 hours (or 72 hours) of culture.

EXAMPLES

Example 1: Optimization of Mucin Replacement Component Composition in Culture Medium Based on soy casein digest broth (tryptic soy broth (TSB)), the optimal combination of substrates and components that can replace mucin was investigated. To this end, an *Akkermansia muciniphila* EB-AMDK19 (KCTC 13761BP) strain was inoculated into each of media prepared at a ratio of 0.1% v/v as shown in Table 1 below, and then cultured at 37° C. under anaerobic conditions (90% $N_2$, 5% $CO_2$, and 5% $H_2$) for 24 to 48 hours, and changes in optical density ($OD_{600}$) thereof were measured. The results of the measurement are shown in Table 1 below.

TABLE 1

| | Mucin (g/L) | Glu (g/L) | GlcNAc (g/L) | Lac (g/L) | Thr (g/L) | Asp (g/L) | Vitamin solution [3] | Growth ($\Delta OD_{600}$)*,† |
|---|---|---|---|---|---|---|---|---|
| PM [1] | — | 4.5 | 5.5 | — | 4 | — | — | 0.133 ± 0.003 |
| TSB [2] | — | 2.5 | — | — | — | — | — | 0.030 ± 0.005 |
| TSB | 2.5 | 2.5 | — | — | — | — | — | 0.368 ± 0.005 |
| TSB | — | 5 | 5 | — | 4 | — | — | 0.289 ± 0.003 |
| TSB | — | 2.5 | 2.5 | 2.5 | 4 | — | — | 0.290 ± 0.003 |

TABLE 1-continued

| | Mucin (g/L) | Glu (g/L) | GlcNAc (g/L) | Lac (g/L) | Thr (g/L) | Asp (g/L) | Vitamin solution [3] | Growth ($\Delta OD_{600}$)*,† |
|---|---|---|---|---|---|---|---|---|
| TSB | — | — | 2.5 | 2.5 | 2.5 | — | 2 | — | 0.291 ± 0.003 |
| TSB | — | — | 2.5 | 2.5 | 2.5 | — | 4 | — | 0.302 ± 0.005 |
| TSB | — | — | 2.5 | 2.5 | 2.5 | — | 6 | — | 0.310 ± 0.004 |
| TSB | — | — | 2.5 | 2.5 | 2.5 | — | 8 | — | 0.338 ± 0.004 |
| TSB | — | — | 2.5 | 2.5 | 2.5 | — | 16 | — | 0.257 ± 0.002 |
| TSB | — | — | 2.5 | 2.5 | 2.5 | — | 8 | + | 0.409 ± 0.006 |

[1] PM: patent medium contains 16 g/L soybean peptone and 10 g/L yeast extract as an amino acid source
[2] TSB (tryptic soy broth): TSB contains 17 g/L casein pancreatic digest, 3 g/L soybean papaic digest, 5 g/L NaCl, and 2.5 g/L $K_2HPO_4$
[3] Vitamin solution contains 0.02 mg/L biotin, 0.2 mg/L niacin, 0.5 mg/L pyridoxine, 0.1 mg/L riboflavin, 0.2 g/L thiamine, 0.1 g/L cyanocobalamin, 0.1 g/L p-aminobenzoic acid, and 0.1 g/L pantothenic acid
Abbreviation: Glu, glucose; GlcNAc, N-acetyl-D-glucosamine, Lac, lactose; Thr, threonine; Asp, aspartic acid It was shown that the *Akkermansia muciniphila* strain was rarely grown in the TSB medium, but could be cultured when N-acetylglucosamine (GlcNAc) and threonine were added as components capable of replacing mucin. However, it was shown that, when threonine was replaced with aspartate, the culturability of the strain was improved at the same concentration (4 g/L), and the culturability increased until aspartate was added to a concentration of up to 8 g/L.

As can be seen in Table 1 above, the change in absorbance in each medium obtained by adding N-acetylglucosamine, lactose, aspartate and vitamin to TSB was found to be about 0.4, and the viable cell count in this medium was measured to be $10^9$ CFU/mL. In comparison with this, the change in absorbance in the PM medium was about 0.1, and the viable cell count in this PM medium was measured to be $10^8$ CFU/mL, which was more than 10 times different from that in the TSB medium.

This is believed to be because the oxaloacetate/aspartate amino acid family consists of lysine, asparagine, methionine, threonine and isoleucine, and aspartate can be converted into lysine, asparagine, methionine and threonine during metabolism.

Example 2: Comparison of Culturability in Media Having Different Carbon Sources In order to exclude an animal-derived component or a component prepared using an animal-derived enzyme, the ability of the medium supplement of the present invention to culture anaerobes was tested based on plant peptone and yeast extract.

Soy peptone as plant peptone and yeast extract were combined with each other at concentrations of 5, 10, 15 and 20 g/L and tested, and as a result, a combination of 20 g/L soy peptone and 10 g/L yeast extract showed the best culturability. In addition, potassium phosphate dibasic for pH adjustment was added at a concentration of 2.5 g/L, thereby preparing basal media.

In order to examine the effect of carbon sources on the culturability of the anaerobe *Akkermansia muciniphila*, various carbon sources were added to each nitrogen source-based medium as shown in Table 2 below, and an *Akkermansia muciniphila* EB-AMDK19 (KCTC 13761BP) strain was inoculated into the medium at a ratio of 0.1% v/v and then cultured at 37° C. under anaerobic conditions (90% $N_2$, 5% $CO_2$, and 5% $H_2$) for 24 to 48 hours. Next, changes in the optical density ($OD_{600}$) of the strain were measured, and the results of the measurement are shown in Table 3 below.

TABLE 2

| Addition of supplement to nitrogen source-based medium (containing the following components per L) | |
|---|---|
| Soy peptone | 20.0 g |
| Yeast extract | 10.0 g |
| Potassium phosphate dibasic | 2.5 g |
| Supplement | |
| N-acetyl-D-glucosamine | 5.0 g |
| D-lactose monohydrate | 2.5 g |
| D-fructose | 2.5 g |
| [Fructose replacement] maltose monohydrate | 2.5 g |
| L-aspartic acid | 8.0 g |
| L-cysteine•hydrochloric anhydride | 0.5 g |
| Cyanocobalamin | 0.1 mg |

TABLE 3

| Soy peptone (g/L) | yeast extract (g/L) | Glu (g/L) | Fru (g/L) | Mal (g/L) | Lac (g/L) | GlcNAc (g/L) | Asp (g/L) | Cobalamin (mg/L) | Growth ($\Delta OD_{600}$)*,† |
|---|---|---|---|---|---|---|---|---|---|
| 20 | 10 | — | — | — | 2.5 | 5 | 8 | 0.1 | 0.506 ± 0.003 |
| 20 | 10 | 2.5 | — | — | 2.5 | 5 | 8 | 0.1 | 0.509 ± 0.003 |
| 20 | 10 | — | 2.5 | — | 2.5 | 5 | 8 | 0.1 | 0.560 ± 0.005 |
| 20 | 10 | — | — | 2.5 | 2.5 | 5 | 8 | 0.1 | 0.527 ± 0.008 |
| 20 | 10 | — | 2.5 | 2.5 | 2.5 | 5 | 8 | 0.1 | 0.529 ± 0.008 |

† $\Delta OD$ was calculated as the difference in absorbance between the initial stage of culture and after 48 hours of culture.

As can be seen from the results in Table 3 above, it was shown that the culturability of the *Akkermansia muciniphila* strain was much better in the medium obtained by adding fructose to the medium based on lactose as a carbon source than in the medium obtained by adding acetylglucosamine or a combination of N-acetylglucosamine and glucose to the lactose-based medium. The change in absorbance (ΔOD) was found to be about 0.5 to 0.6 on average, and the viable cell count was measured to be about $10^{10}$ CFU/mL. Thus, it was confirmed that the viable cell count in the medium of the present invention increased 10 to 100 times, indicating that the culturability in the medium of the present invention was significantly improved. In addition, when maltose to which two glucose molecules are linked by β(1→4)-glycosidic bonds was added, the culturability was improved compared to when glucose was added.

Example 3: Selection of Group B Vitamin Important for Improvement in Culturability In this Example, whether the addition of group B vitamin to the medium for culture of the *Akkermansia muciniphila* strain improved culturability was examined. In order to select specific vitamins influencing the growth of anaerobes, tests were performed for each of all vitamins (B1, B2, B3, B5, B6, B7, B9, B10, and B12) belonging to the vitamin B group or for vitamin B complexes.

As shown in Table 4 below, the *Akkermansia muciniphila* strain was inoculated into each prepared medium at a ratio of 0.1% v/v, and then cultured at 37° C. under anaerobic conditions (90% $N_2$, 5% $CO_2$, and 5% $H_2$) for 24 to 48 hours, and changes in the optical density ($OD_{600}$) of the strain were measured. The results of the measurement are shown in Table 4 below.

As can be seen from the results in Table 4 above, it was confirmed that the culturability increased only when cobalamin (vitamin B12) was contained in the media (B12, or B2+B6+B9+B12, B1+B2+B3+B5+B6+B7+B9+B12, or B1+B2+B3+B5+B6+B7+B9+B10+B12), and there was no significant difference between the addition of vitamin B12 alone and the addition of vitamin B complexes.

In addition, to find the optimal concentration of cobalamin, the strain was cultured while changing the concentrations of cobalamin, and then changes in the optical density ($OD_{600}$) of the strain were measured. The results of the measurement are shown in Table 5 below.

TABLE 5

| Cyanocobalamin (mg/L) | Growth ($AOD_{600}$) [*,†] | P value [‡] |
|---|---|---|
| — | 0.326 ± 0.008 | — |
| 0.05 | 0.563 ± 0.012 | <0.0001 |
| 0.1 | 0.576 ± 0.014 | <0.0001 |
| 0.2 | 0.577 ± 0.008 | <0.0001 |
| 0.5 | 0.575 ± 0.011 | <0.0001 |
| 1 | 0.581 ± 0.003 | <0.0001 |
| 5 | 0.571 ± 0.007 | <0.0001 |

[†] ΔOD was measured as the difference in absorbance between the initial stage of culture and after 48 hours of culture.

As can be seen from the results in Table 5 above, as a result of performing the experiment to find the optical concentration of vitamin B12 that was added to the medium, it was confirmed that, at a vitamin B12 concentration lower than 0.1 mg/L, the culturability decreased gradually, and at a vitamin B12 concentration ranging from 0.1 mg/L to 5 mg/L, no significant difference in the culturability appeared, indicating that a vitamin B12 concentration of 0.1 mg/L was the optimal concentration.

Example 4: Optimization of Medium Components

In order to find the essential components necessary for high-concentration culture of anaerobes and an optimal combination thereof, the *Akkermansia muciniphila* strain was cultured in media having various combinations of components under the same conditions. The results are shown in Table 6 below.

TABLE 4

| B1 (mg/L) | B2 (mg/L) | B3 (mg/L) | B5 (mg/L) | B6 (mg/L) | B7 (mg/L) | B9 (mg/L) | B10 (mg/L) | B12 (mg/L) | Growth ($\Delta OD_{600}$) [*,†] | P value [†] |
|---|---|---|---|---|---|---|---|---|---|---|
| — | — | — | — | — | — | — | — | — | 0.331 ± 0.003 | — |
| 0.2 | — | — | — | — | — | — | — | — | 0.352 ± 0.003 | 0.0698 |
| — | 0.1 | — | — | — | — | — | — | — | 0.334 ± 0.009 | 0.9994 |
| — | — | 0.2 | — | — | — | — | — | — | 0.342 ± 0.018 | 0.9732 |
| — | — | — | 0.1 | — | — | — | — | — | 0.347 ± 0.005 | 0.4077 |
| — | — | — | — | 0.5 | — | — | — | — | 0.337 ± 0.014 | 0.9869 |
| — | — | — | — | — | 0.02 | — | — | — | 0.344 ± 0.008 | 0.3570 |
| — | — | — | — | — | — | 0.05 | — | — | 0.348 ± 0.013 | 0.7130 |
| — | — | — | — | — | — | — | 0.1 | — | 0.335 ± 0.009 | 0.9999 |
| — | — | — | — | — | — | — | — | 0.1 | 0.575 ± 0.018 | 0.0124 |
| — | 0.1 | — | — | 0.15 | — | 0.05 | — | 0.1 | 0.582 ± 0.020 | 0.0121 |
| 0.2 | 0.1 | 0.2 | 0.1 | 0.15 | 0.01 | 0.05 | — | 0.1 | 0.561 ± 0.014 | 0.0119 |
| 0.2 | 0.1 | 0.2 | 0.1 | 0.15 | 0.01 | 0.05 | 0.1 | 0.1 | 0.585 ± 0.010 | 0.0019 |

[†] ΔOD was calculated as the difference in absorbance between the initial stage of culture and after 72 hours of culture.

TABLE 6

| Soy peptone (g/L) | Yeast extract (g/L) | Mucin (g/L) | Fru (g/L) | Mal (g/L) | Lac (g/L) | GlcNAc (g/L) | Asp (g/L) | Cobalamin (mg/L) | Growth ($\Delta OD_{600}$) [*,†] |
|---|---|---|---|---|---|---|---|---|---|
| 20 | 10 | 2.5 | — | — | — | — | — | — | 0.148 ± 0.002 |
| 20 | 10 | — | 2.5 | — | 2.5 | 5 | 8 | 0.1 | 0.539 ± 0.004 |
| 20 | 10 | — | 5 | — | 2.5 | 5 | 8 | 0.1 | 0.533 ± 0.015 |
| 20 | 10 | — | — | 2.5 | 2.5 | 5 | 8 | 0.1 | 0.525 ± 0.011 |
| 20 | 10 | — | — | 5 | 2.5 | 5 | 8 | 0.1 | 0.512 ± 0.012 |
| 20 | 10 | — | — | — | 2.5 | 5 | 8 | 0.1 | 0.505 ± 0.005 |
| 20 | 10 | — | 2.5 | — | — | 5 | 8 | 0.1 | 0.428 ± 0.013 |
| 20 | 10 | — | 2.5 | — | 2.5 | — | 8 | 0.1 | 0.004 ± 0.001 |
| 20 | 10 | — | 2.5 | — | 2.5 | 5 | — | 0.1 | 0.324 ± 0.002 |
| 20 | 10 | — | 2.5 | — | 2.5 | 5 | 8 | — | 0.387 ± 0.006 |
| 20 | — | — | 2.5 | — | 2.5 | 5 | 8 | 0.1 | 0.533 ± 0.005 |
| — | 10 | — | 2.5 | — | 2.5 | 5 | 8 | 0.1 | 0.350 ± 0.008 |
| 20 | 10 | — | — | — | — | 5 | — | — | 0.242 ± 0.004 |
| 20 | 10 | — | 2.5 | — | — | — | — | — | 0.004 ± 0.001 |
| 20 | 10 | — | — | — | 2.5 | — | — | — | 0.002 ± 0.002 |
| 20 | 10 | — | 2.5 | — | 2.5 | — | — | — | 0.003 ± 0.002 |
| 20 | 10 | — | 2.5 | — | — | 5 | — | — | 0.231 ± 0.003 |
| 20 | 10 | — | — | — | 2.5 | 5 | — | — | 0.283 ± 0.004 |
| 20 | 10 | — | 2.5 | — | 2.5 | 5 | — | — | 0.261 ± 0.002 |

[*] The optical density (O.D.) of each culture sample was measured at λ = 600 nm using a microplate reader.
[†] AOD was calculated as the difference in absorbance between the initial stage of culture and after 48 hours of culture.

As a result of examining the effect of each component on culture in the medium of the present invention, it was confirmed that, in the above-described combinations, N-acetylglucosamine that was a nitrogen-containing derivative of monosaccharide was identified as the most essential component for culture of *Akkermansia muciniphila*, and N-acetylglucosamine and fructose and lactose, which were carbon sources that shared a part of the metabolic pathway, were necessary components for high-concentration culture. In addition, it was confirmed that a combination of soy peptone, aspartate and cyanocobalamin, which were major sources of amino acids, was important for improving the culturability.

Maltose was able to replace glucose or fructose, and the growth rate at the beginning of culture was higher in the medium containing maltose than that in the medium containing fructose or glucose, and there was no significant difference in culturability between the two media. However, at present, maltose is somewhat expensive compared to fructose or glucose, and hence fructose is considered the most suitable industrial medium component. In conclusion, as can be seen in Table 6, all the components of the medium of the present invention are necessary for high-concentration culture of the *Akkermansia muciniphila* strain, and the combination of all the components exhibits the best culturability.

Example 5: Examination of Culturabilities of Various *Akkermansia muciniphila* in Medium of the Present Invention An experiment was performed in the same manner as in Example 1 above, except that the medium shown in Table 2 above were used and the kind of strain cultured was changed as shown in Table 7 below. Specifically, each *Akkermansia muciniphila* strain was inoculated into the medium at a ratio of 0.1% v/v, and then cultured at 37° C. under anaerobic conditions (90% $N_2$, 5% $CO_2$, and 5% $H_2$) for 24 to 48 hours. Changes in the optical density ($OD_{600}$) of each strain were measured, and the results of the measurement are shown in Table 7 below.

TABLE 7

| Test strains | Growth (AOD $_{600}$) [*,†] |
|---|---|
| *Akkermansia muciniphila* ATCC BAA-835[T] | 0.548 ± 0.008 |
| *Akkermansia muciniphila* EB-AMDK19 (KCTC 13761BP) | 0.540 ± 0.012 |
| *Akkermansia muciniphila* EB-AMDK27 (KCTC 13758BP) | 0.535 ± 0.011 |
| *Akkermansia muciniphila* EB-AMDK39 (KCTC 13765BP) | 0.548 ± 0.005 |

As can be seen from the results in Table 7 above, as a result of examining the culturabilities of the *Akkermansia muciniphila* standard strain (ATCC BAA-835 T) and different *Akkermansia muciniphila* strains using the medium of the present invention, it could be confirmed that the medium of the present invention showed similar culture levels for all the *Akkermansia muciniphila* strains, and thus can be used as a medium for high-concentration culture of all the *Akkermansia muciniphila* strains.

Example 6: Comparison of Culturabilities of Various Fastidious Strict Anaerobic Microorganisms An experiment was performed in the same manner as in Example 1, except that the kind of strain cultured was changed as shown in Table 8 below. Specifically, a *Faecalibacterium prausnitzii, Anaerostipes caccae*, or *Bifidobacterium longum* strain was inoculated into the medium of the present invention at a ratio of 0.1% v/v, and then cultured at 37° C. under anaerobic conditions (90% $N_2$, 5% $CO_2$, and 5% $H_2$) for 24 to 48 hours. Then, changes in the optical density ($OD_{600}$) of each strain were measured, and the results of the measurement are shown in Table 8 below. For comparison, each of the strains was also cultured in control media known to show excellent culturability, and the culturability of each strain in the control media was compared with the culturability in the medium of the present invention. Specifically, *F. prausnitzii* was cultured in a brain heart infusion (BHI) medium (supplemented with 5 g/L yeast extract, 1 g/L cellobiose and 1 g/L maltose) as a control medium. *A. caccae* was cultured in a TSB medium supplemented with 5 g/L yeast extract, and *B. longum* was cultured in BL broth.

TABLE 8

| Anaerobes | Culturability (AOD$_{600}$) *,† | |
|---|---|---|
| | Control media [1] | Medium of the present invention (containing the components shown in Table 1) |
| *Faecalibacterium prausnitzii* EB-FPDK11 (KCCM 1262IP) | 0.105 ± 0.002 | 0.307 ± 0.006 |
| *Anaerostipes caccae* LI-92$^T$ | 0.364 ± 0.003 | 0.463 ± 0.003 |
| *Bifidobacterium longum* EB-BGYK18 (KCCM 12626P) | 0.304 ± 0.003 | 0.333 ± 0.002 |

[1]Control medium for culture of *F. prausnitzii*: Brain heart infusion (BHI) medium supplemented with 5 g/L yeast extract, 1 g/L cellobiose and 1 g/L maltose
Control medium for culture of *A. caccae*: TSB medium supplemented with 5 g/L yeast extract
Control medium for culture of *B. longum*: BL broth As can be seen from the results in Table 8 above, as a result of testing the culturabilities of fastidious strict anaerobic microorganisms such as *Faecalibacterium prausnitzii, Anaerostipes caccae* and *Bifidobacterium longum*, it was confirmed that the culturabilities of the strains in the medium of the present invention were better than those in the control media known to show excellent culturability.

Figure 4:
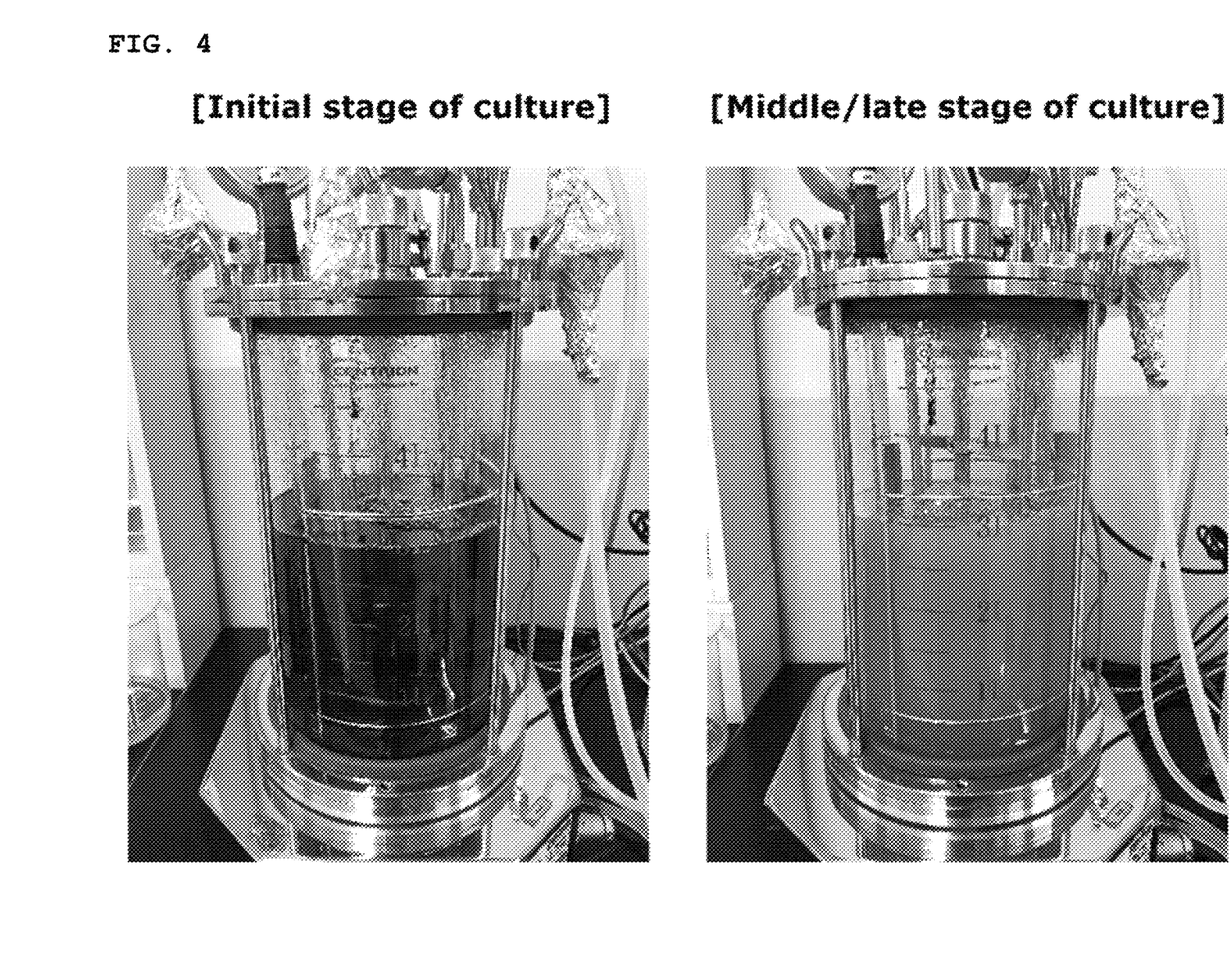
FIG. 4 depicts photographs showing culture time-dependent changes in the color of a medium in which an *Akkermansia muciniphila* strain has been cultured in an Example of the present invention.
Figure 5:
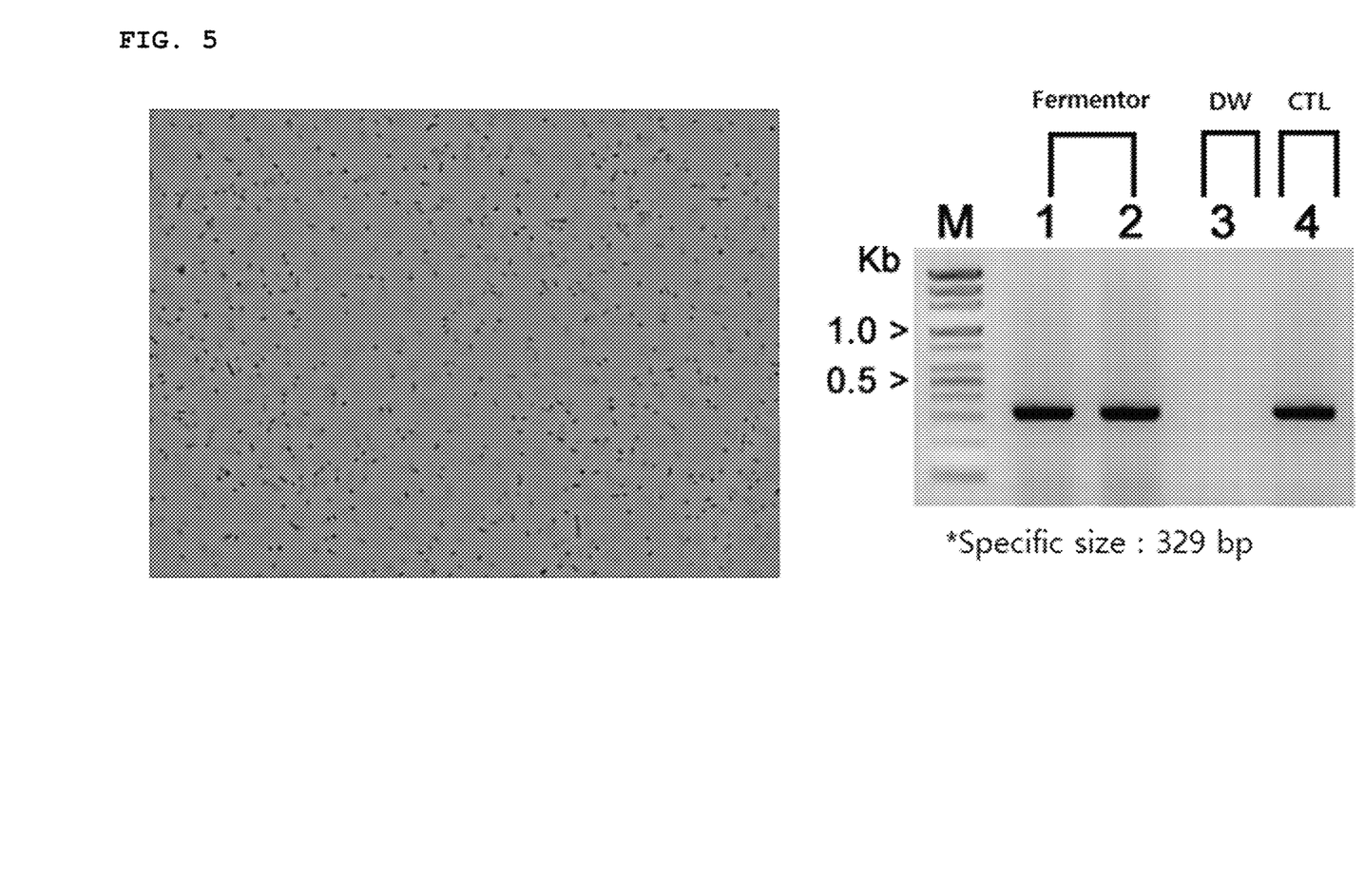
FIG. 5 shows the result of microscopic observation of *Akkermansia muciniphila* and the result of analyzing the culture of a culture through the results of PCR analysis performed using specific primers.

Example 7: Optimization of Process Conditions for Mass Culture—Comparative Analysis of Culturability Under Each Culture Condition Using a 3 L-scale anaerobic fermentation system shown in FIG. 4 and each medium obtained by changing the kind of carbon source in the medium of Table 2, culture was performed under the conditions shown in Table 9 below. A growth curve of the *Akkermansia muciniphila* strain was obtained, and changes in the pH thereof were examined. In addition, changes in the number of microbial cells and morphological changes thereof were examined through microscopic observation, and the results are shown in FIG. 5. In addition, the number of viable cells was counted using a plate count method, and the results are shown in Table 10 below.

TABLE 9

| Culture temperature | 37 ± 1° C. |
|---|---|
| pH | 6.8 ± 0.2 |
| Gas flow(100% N$_2$ or 90% N$_2$, 5% CO$_2$, and 5% H$_2$) | 0.2 liters/hr |
| Agitation speed | 40 to 50 rpm |
| Inoculum | 1% v/v |
| Incubator size | 3 L |

TABLE 10

| | Example [1] | Example [2] | Comparative Example [3] | Comparative Example [4] |
|---|---|---|---|---|
| Carbon source | Fructose | Maltose | Fructose | Fructose |
| Gas composition in incubator | 90% N$_2$, 5% CO$_2$, 5% H$_2$ | 90% N$_2$, 5% CO$_2$, 5% H$_2$ | 100% N$_2$ | 80% N$_2$, 20% CO$_2$ |
| OD$_{600}$ (ELISA) | 0.798 ± 0.004 | 0.632 ± 0.011 | 0.105 ± 0.001 | 0.640 ± 0.005 |
| Viable cell count (CFU/mL) | 5.5 × 10$^{10}$ | 5.1 × 10$^{10}$ | ≥10$^8$ | 5 × 10$^{10}$ |

Figure 6A:
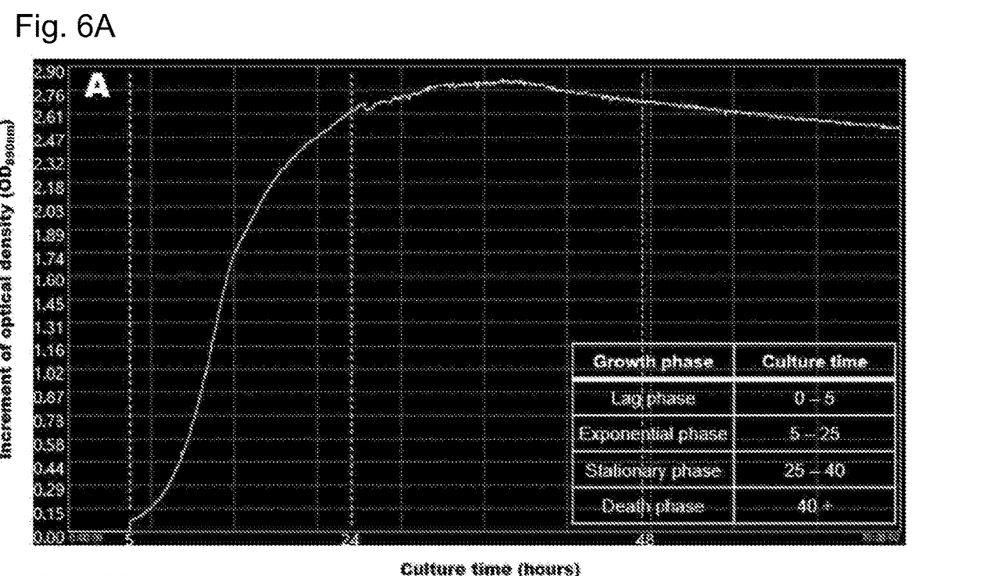
Figure 6B:
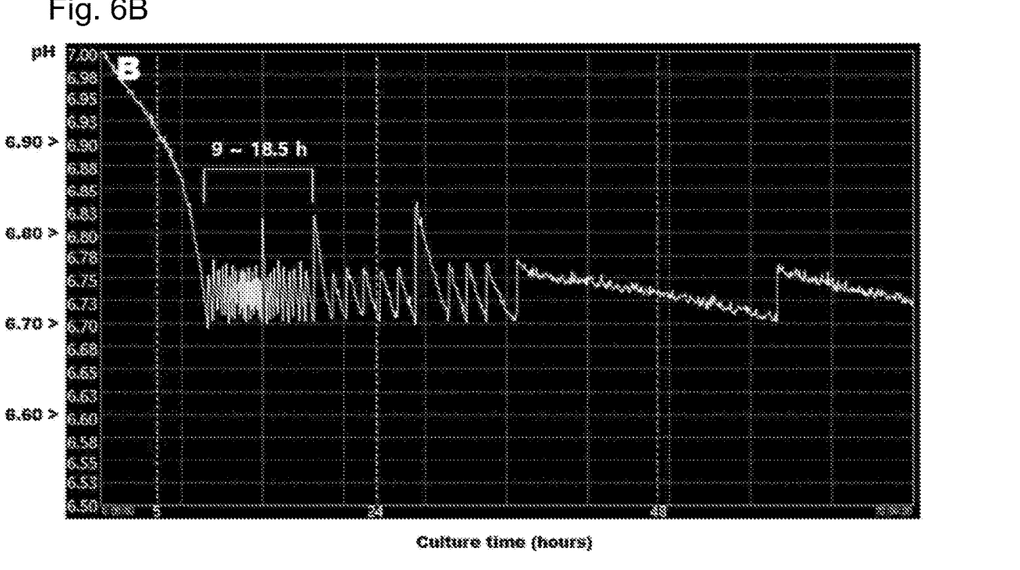

[1] Fructose-containing medium of the present invention: 20 g/L soy peptone, 10 g/L yeast extract, 2.5 g/L K$_2$HPO$_4$, 5 g/L GlcNAc, 2.5 g/L lactose, 8 g/L aspartic acid, 0.1 mg/L cyanocobalamin, and 2.5 g/L fructose
[2] Maltose-containing medium of the present invention: 20 g/L soy peptone, 10 g/L yeast extract, 2.5 g/L K$_2$HPO$_4$, 5 g/L GlcNAc, 2.5 g/L lactose, 8 g/L aspartic acid, 0.1 mg/L cyanocobalamin, and 2.5 g/L maltose
[3] High-purity nitrogen gas (100% N$_2$) was used instead of mixed gas (90% N$_2$, 5% CO$_2$, and 5% H$_2$)
[4] Mixed gas consisting of 80% N$_2$ and 20% CO$_2$ was used As a result of culturing the *Akkermansia muciniphila* EB-AMDK19 strain in the anaerobic fermentation system using the medium of the present invention, it was confirmed that the exponential phase of the strain occurred at 5 to 25 hours after inoculation and that the change in pH occurred rapidly at 9 to 18.5 hours after inoculation. At 24 hours of culture, the optical density (OD$_{600}$) was found to be about 0.798, and the viable cell count at this time was measured to be 5.5×10$^{10}$ CFU/mL (see FIG. 6 and Table 10).

Figure 7A:
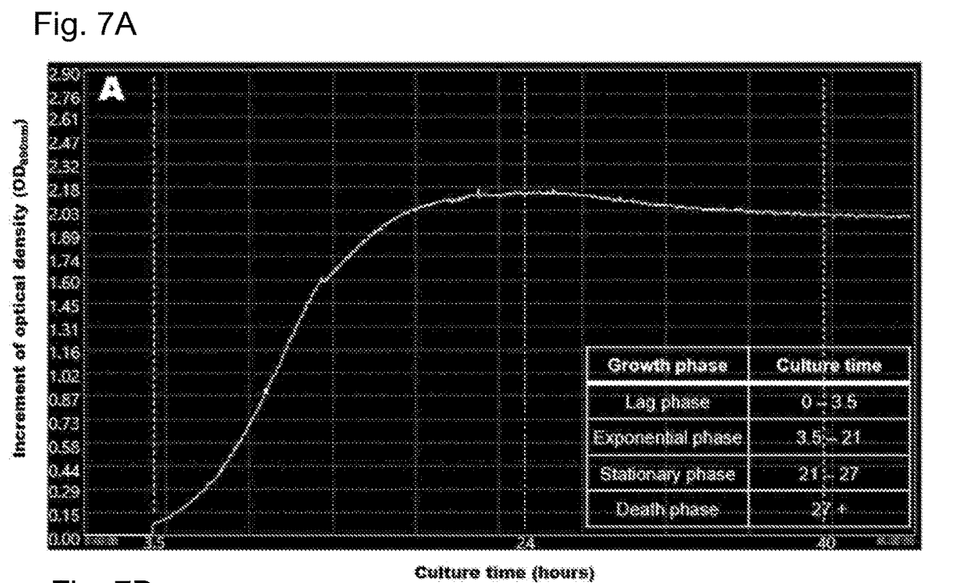
Figure 7B:
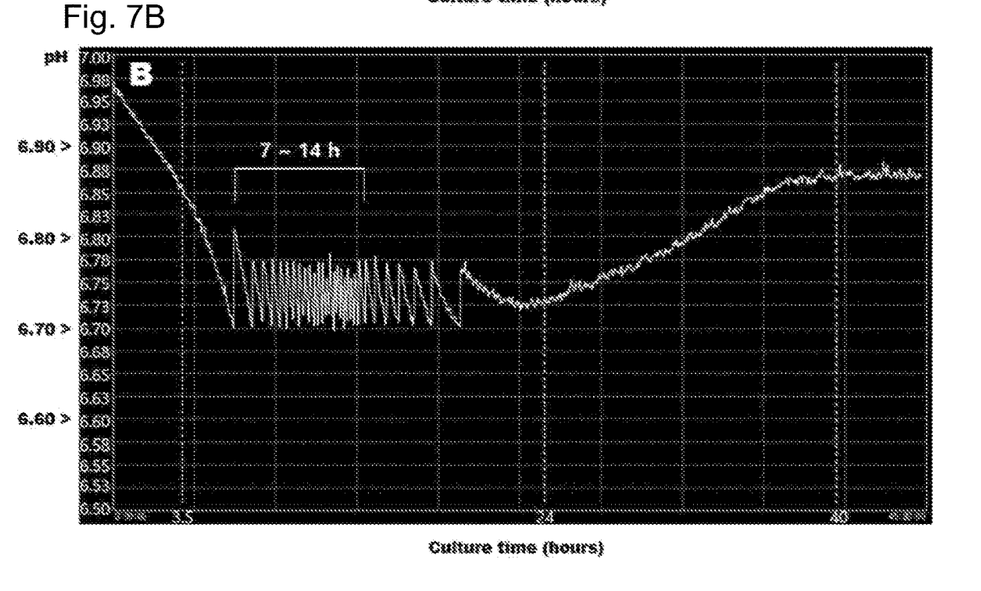

It was confirmed that, when fructose in the medium of the present invention was replaced with maltose, the exponential phase of the strain occurred at 3.5 to 21 hours after inoculation and that the change in pH occurred rapidly at 7 to 14 hours after inoculation. When comparing the results of culturing the strain using the medium containing fructose, the lag phase in the maltose-containing medium of the present invention was shortened by 1.5 hours. At 24 hours of culture, the absorbance in the maltose-containing medium was about 0.632, which was slightly lower than that in the fructose-containing medium, but the viable cell count at this time was 5.1×10$^{10}$ CFU/mL, which did significantly differ from that in the fructose-containing medium (see FIG. 7 and Table 9).

Figure 8A:
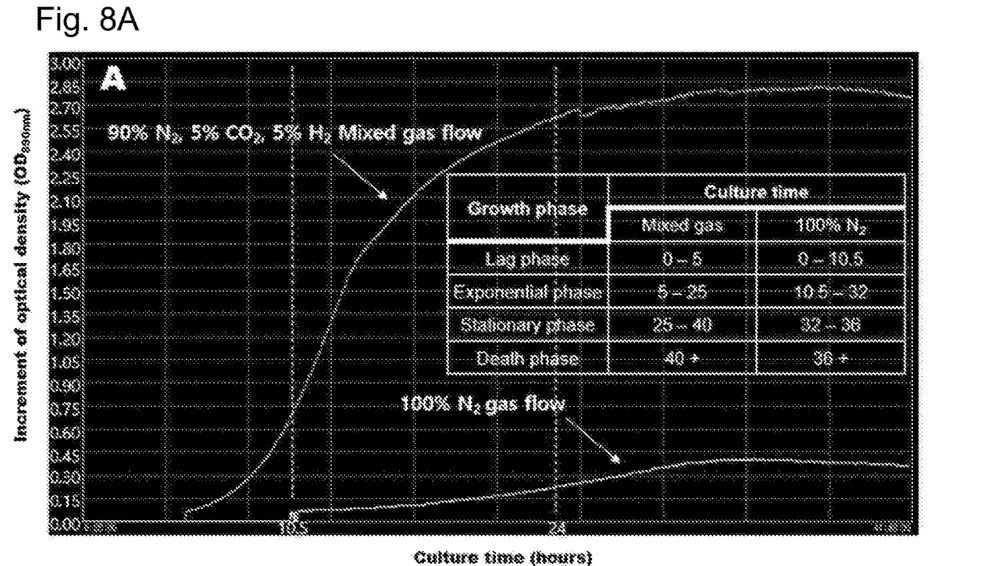
Figure 8B:
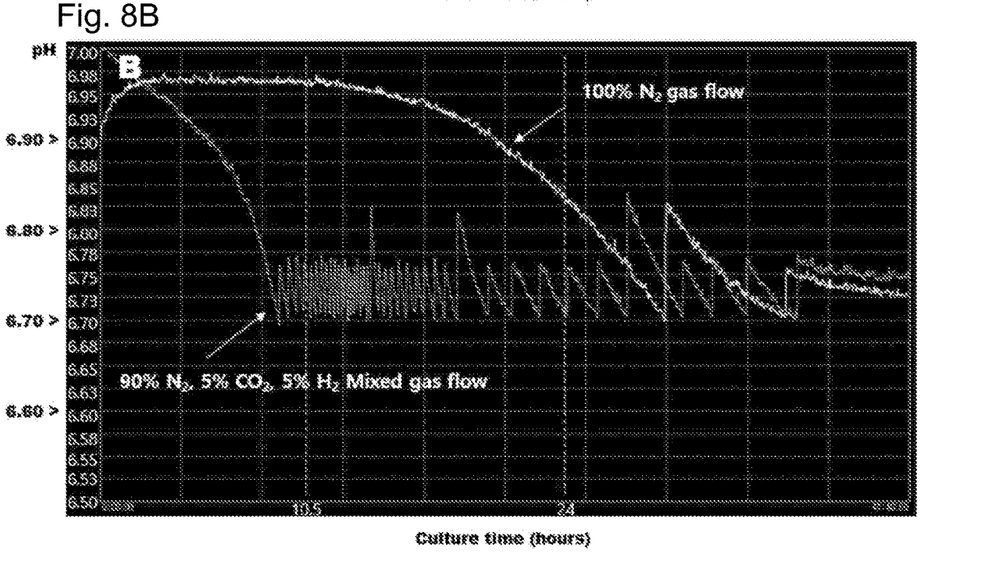

As a result of culturing the strain in the fructose-containing medium of the present invention using a hydrogen-free gas (a high-purity nitrogen gas (100% N$_2$) or a mixed gas consisting of 80% N$_2$ and 20% CO$_2$), which is more economical and suitable for industrialization, instead of a mixed gas (90% N$_2$, 5% CO$_2$, and 5% H$_2$), it was shown that the culturability in the high-purity nitrogen gas was significantly lower than that in conventional culture, but the culturability in the gas consisting of 80% N$_2$ and 20% CO$_2$ did not significantly differ from that in conventional culture (see FIG. 8 and Table 10).

In addition, as can be seen from the results in Table 10 above, it was found that all the components in the medium of the present invention are necessary for high-concentration culture of the *Akkermansia muciniphila* strain and that injection of a mixed gas containing hydrogen or carbon dioxide is additionally necessary for high-concentration culture of the *Akkermansia muciniphila* strain.

The invention claimed is:

1. A medium composition for culture of anaerobes, the medium composition comprising: plant peptone; yeast extract; potassium phosphate dibasic; as a carbon source, fructose and lactose; and as supplements, N-acetylhexosamine, an amino acid mixture of L-aspartic acid and L-cysteine, and cobalamin,
    wherein the anaerobes are selected from the group consisting of *Faecalibacterium prausnitzii, Anaerostipes caccae, Akkermansia muciniphila*, and *Bifidobacterium longum*.

2. The medium composition of claim 1, containing 20 g/L of plant peptone, 10 g/L of yeast extract, 2.5 g/L of potassium phosphate dibasic, 2.5 g/L of fructose, 2.5 g/L of lactose, 5 g/L of N-acetylhexosamine, 8 g/L of L-aspartic acid, 0.5 g/L of L-cysteine, and 0.0001 to 0.005 g/L of cobalamin.

3. The medium composition of claim 1, wherein the plant peptone is selected from the group consisting of soy peptone, wheat peptone, cotton peptone, pea peptone, broadbean peptone, lupin peptone, and potato peptone.

4. The medium of claim 1, wherein the anaerobes are *Faecalibacterium prausnitzii* or *Akkermansia muciniphila*.

5. A method for culturing anaerobes, the method comprising inoculating anaerobes into the medium composition of claim 1 and culturing the inoculated anaerobes under anaerobic conditions.

6. The method of claim 5, wherein the culturing is performed under conditions of a pH of 6.6 to 7.0, a culture temperature of 35 to 39° C., an agitation speed of 40 to 50 rpm, a nitrogen saturation degree of 80 to 90%, a hydrogen saturation degree of 0 to 5%, and a carbon dioxide saturation degree of 5 to 20%.

7. The method of claim 5, wherein the cultured anaerobes reaches a cell density corresponding to a viable cell count of $10^{10}$ CFU/mL or more as measured by a plate count method.

8. The method of claim 5, wherein the nitrogen saturation degree is 80%, a hydrogen saturation degree is 0%, and a carbon dioxide saturation degree is 20%.

9. The method of claim 5, wherein the anaerobes are *Faecalibacterium prausnitzii* or *Akkermansia muciniphila*.

10. A method for culturing anaerobes, the method comprising inoculating anaerobes into the medium composition of claim 2 and culturing the inoculated anaerobes under anaerobic conditions.

11. A method for culturing anaerobes, the method comprising inoculating anaerobes into the medium composition of claim 3 and culturing the inoculated anaerobes under anaerobic conditions.

\* \* \* \* \*